(12) United States Patent
Stirn et al.

(10) Patent No.: US 12,264,206 B2
(45) Date of Patent: Apr. 1, 2025

(54) METHOD AND DEVICE FOR THE DIGESTION OF STARCH

(71) Applicant: PGA PUTZ-GRANITZER-ANLAGENBAU GESELLSCHAFT M.B.H., Wernberg (AT)

(72) Inventors: Christian Stirn, Puch (AT); Roman Steindl, Zwettl (AT); Klaus Bartelmuss, Teufenbach-Katsch (AT)

(73) Assignee: PGA PUTZ-GRANITZER-ANLAGENBAU GESELLSCHAFT M.B.H., Wernberg (AT)

( * ) Notice: Subject to any disclaimer, the term of this patent is extended or adjusted under 35 U.S.C. 154(b) by 1010 days.

(21) Appl. No.: 17/283,905

(22) PCT Filed: Oct. 8, 2019

(86) PCT No.: PCT/EP2019/077149
§ 371 (c)(1),
(2) Date: Apr. 8, 2021

(87) PCT Pub. No.: WO2020/074471
PCT Pub. Date: Apr. 16, 2020

(65) Prior Publication Data
US 2022/0010034 A1 Jan. 13, 2022

(30) Foreign Application Priority Data
Oct. 8, 2018 (AT) .................................... 313/2018

(51) Int. Cl.
*C08B 30/12* (2006.01)
*B01F 23/50* (2022.01)
(Continued)

(52) U.S. Cl.
CPC ............ *C08B 30/12* (2013.01); *B01F 23/511* (2022.01); *B01F 27/808* (2022.01);
(Continued)

(58) Field of Classification Search
None
See application file for complete search history.

(56) References Cited

U.S. PATENT DOCUMENTS 3,308,037 A 3/1967 Goos et al.
3,371,018 A 2/1968 Ewing et al.
(Continued)

FOREIGN PATENT DOCUMENTS

AT 516103 A1 2/2016
CH 513 980 10/1971
(Continued)

OTHER PUBLICATIONS

Office Action issued in Japanese Patent Application No. 2021-519565 dated Aug. 31, 2022.
(Continued)

*Primary Examiner* — John J Figueroa
(74) *Attorney, Agent, or Firm* — NIXON & VANDERHYE

(57) ABSTRACT

With a method for digesting starch, an aqueous slurry of the starch is treated with steam in a cooking vessel and in this case exposed to shear forces, wherein the starch-containing slurry is heated to a temperature of between 85°C and 110°C in the cooking vessel by introducing steam, and the digestion step is implemented until the desired degree of digestion has been reached. Also described is a cooking vessel that can be used when the method for digesting starch is being carried out.

16 Claims, 9 Drawing Sheets

Figure 1:
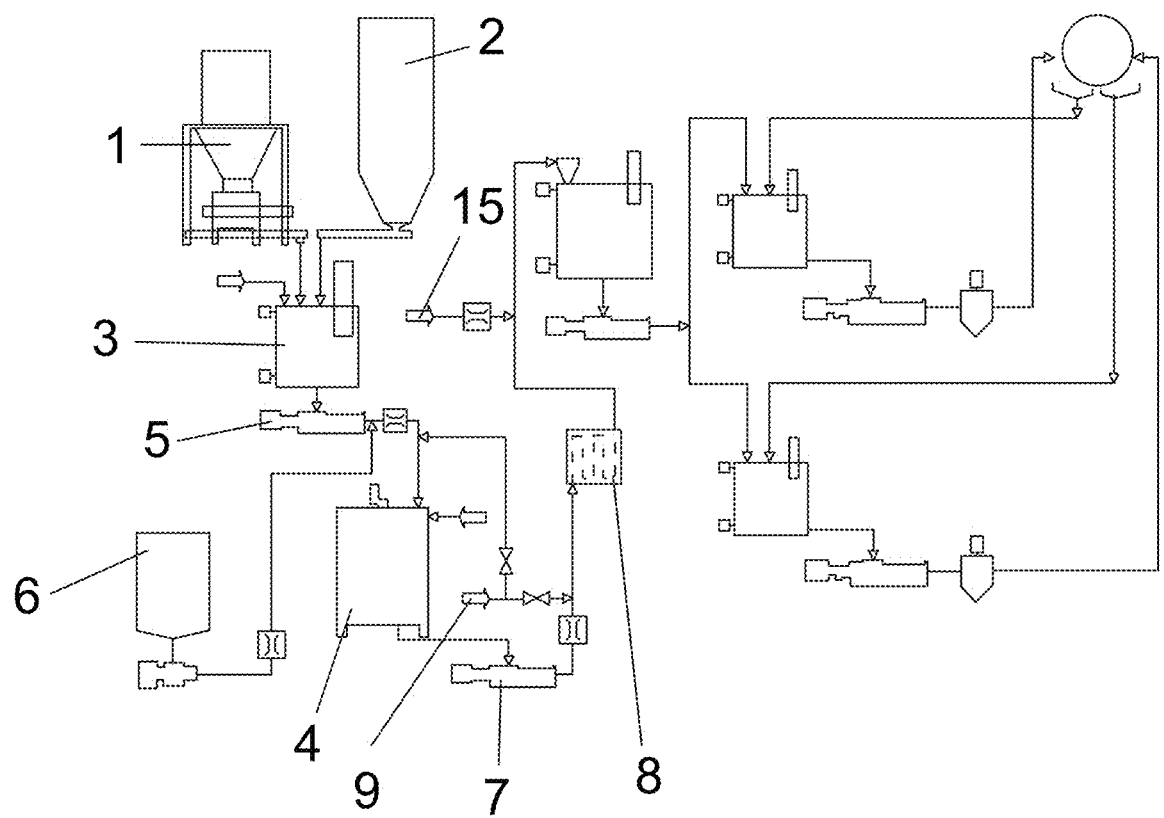

(51) Int. Cl.
  *B01F 27/808* (2022.01)
  *B01F 27/81* (2022.01)
  *C08B 30/16* (2006.01)
  *C12P 19/22* (2006.01)
(52) U.S. Cl.
  CPC .......... *B01F 27/8111* (2022.01); *C08B 30/16* (2013.01); *C12P 19/22* (2013.01)

(56) References Cited

U.S. PATENT DOCUMENTS

| | | | |
|---|---|---|---|
| 4,667,654 A * | 5/1987 | Thaler | F26B 3/12 127/65 |
| 5,188,674 A * | 2/1993 | Kasica | C08J 3/122 127/65 |
| 5,318,635 A * | 6/1994 | Kasica | C08B 30/14 127/65 |
| 5,437,169 A | 8/1995 | Mitchell et al. | |
| 2006/0204569 A1* | 9/2006 | Obae | C08B 30/12 424/70.13 |
| 2010/0092614 A1 | 4/2010 | Bauer | |
| 2010/0159104 A1* | 6/2010 | Bastien | C08B 30/16 426/578 |

FOREIGN PATENT DOCUMENTS

| | | |
|---|---|---|
| CN | 101405302 A | 4/2009 |
| CN | 101668864 A | 3/2010 |
| CN | 205917199 U | 2/2017 |
| CN | 205999716 U | 3/2017 |
| CN | 206014739 U | 3/2017 |
| DE | 10 2007 011 409 | 9/2008 |
| FR | 2 322 925 A1 | 4/1977 |
| GB | 1193549 A | 6/1970 |
| JP | S7-027943 B | 7/1972 |
| JP | 2009-530467 A | 8/2009 |
| RU | 2462477 C1 | 9/2012 |
| RU | 2654248 C2 | 5/2018 |
| SU | 1407954 A1 | 7/1988 |
| WO | 2018/011401 | 1/2018 |

OTHER PUBLICATIONS

Office Action issued in Chinese Patent Application No. 201980066207.X dated Mar. 15, 2022.
Office Action issued in Canadian Patent Application No. 3,115,723 dated Mar. 29, 2023.
International Search Report for PCT/EP2019/077149 dated Jan. 24, 2020, 9 pages.
Written Opinion of the ISA for PCT/EP2019/077149 dated Jan. 24, 2020, 5 pages.
AT Search Report for At A 313/2018 dated Jul. 5, 2019, 1 page.
Search Report issued in Russian Patent Application No. 2021112139/10(025956) dated Dec. 22, 2021 with English Machine Translation provided.
Guglielmo et al., "Development and testing of a novel lab-scale direct steam-injection apparatus to hydrolyse model and saline crop slurries," Journal of Biotechnology, vol. 157, 2012, pp. 590-597.

* cited by examiner

METHOD AND DEVICE FOR THE DIGESTION OF STARCH

CROSS-REFERENCE TO RELATED APPLICATIONS

This application is the U.S. national phase of International Application No. PCT/EP2019/077149 filed Oct. 8, 2019 which designated the U.S. and claims priority to AT A 313/2018 filed Oct. 8, 2018, the entire contents of each of which are hereby incorporated by reference.

BACKGROUND OF THE INVENTION

Field of the Invention

The invention relates to a method for digesting starch.
The invention also relates to a device that can be used as a cooking vessel when the method according to the invention is being carried out.

Description of the Related Art

Methods for processing starch by breaking starch down are known. In a method for enzymatic breakdown of starch, the native starch powder is fed from supply bags ("BigBags") or silos into a slurry station, in which the starch powder is introduced into water and a slurry (suspension) with up to 35% solid content is created. From the slurry station, the slurry of starch that is thus obtained is pumped into a cooking vessel, wherein the enzyme that causes the breakdown (an amylase) is added in measured quantities in the slurry station or in front of or behind the pump, which conveys slurry from the slurry station to a cooking vessel. Usually, when the slurry is put into the cooking vessel by means of the injection of steam, the slurry is heated to a temperature of 85° C. to 95° C., wherein a breakdown already occurs.

In the feed to the cooking vessel, static mixers or other components can be provided in order to prevent slurry from shooting through and/or to configure the feed of the slurry to be more homogeneous.

In the cooking vessel, with the known method, the dwell time for the desired degree of breakdown is set by means of volume buffering. In the case of various devices for implementing the known method for enzymatic breakdown of starch (native starch), stirring mechanisms and optionally mixer-disks are provided in the cooking vessel in order to accelerate the method.

The paste that is obtained by the digestion of starch is drawn off from the cooking vessel using a pump and—if enzymes were used—pumped through a deactivation zone. Usually, the deactivation zone is a plug flow reactor, in which at the beginning, the paste is heated to a temperature of between 120° C. and 135° C. by introducing steam. The deactivation time is controlled by the pipe volume and/or the pumping power.

After the breakdown of the starch by deactivation of the enzyme has been stopped, paste is diluted again and then stored.

Another known approach is to use, instead of a cooking vessel, a labyrinth pipe, which is installed after the steam injection, wherein a dwell time can be achieved that is sufficient for the desired degree of breakdown, and via shear edges, an additional shearing of the substance in suspension is achieved.

The cooking vessel can also be used in batch operation—if it is made accordingly large enough—with the known method.

It is disadvantageous with the known method that relatively large units are necessary or only small throughput amounts can be obtained.

With a known method for digesting cationic starch, the cationic starch powder is fed from supply bags (BigBags) or silos into a slurry station, and the powder is introduced into water, wherein a slurry (suspension) with up to 15% solid content is created. The starch slurry is pumped into a cooking tube.

With the known method for digesting cationic starch, the cooking tube is a plug flow reactor, in which at the beginning, the starch slurry is heated to 115° C. to 135° C. by introducing steam. The dwell time is controlled by the volume of the plug flow reactor and/or the pumping power. After the cooking process, in most cases, it is diluted again, and the paste that is obtained is then stored.

Also, in the case of the digestion of cationic starch, a labyrinth pipe instead of the cooking tube can be used after the steam injection.

Also, it is known to replace the cooking tube by a cooking vessel, which—if it is made large enough—can also be used in batch operation.

Equipment and methods for breaking starch down are known from U.S. Pat. No. 3,371,018 A, WO 2018/011401 A1, and CH 513 980 A.

It is known from U.S. Pat. No. 3,371,018 A to convert starch into a composition for the paper industry with use of bacterial alpha-amylase (α-amylase) in water under the action of heat (225-350° F.). A vertical reactor column, in which a rotor with propeller blades rotates, is used. Horizontal and vertical baffles are provided. A stirring action with a flow that is directed upward is to be generated. U.S. Pat. No. 3,371,018 A relates to the continuous conversion of starch by bacterial amylases in order to obtain a product that can be used in the paper industry for sizing paper. A vertical reactor with baffles and a stirring mechanism, which is to produce a turbulent flow, is used. Steam is to be introduced to deactivate added amylase, wherein the place where steam is introduced is left open.

WO 2018/011401 A1 describes an enzymatic hydrolysis of starch. The starch that is to be hydrolyzed, to which enzyme is added, is to be subjected to shear forces during mixing. A method for creating hydrolyzed starch, in which an amylotlyic enzyme is used, is disclosed in WO 2018/011401 A1. The required water can be fed as steam (direct steam injection), wherein steam is to be fed by "suitable means." It is mentioned that setting the temperature can be implemented simultaneously with "shear mixing," when hydrolyzation is carried out.

According to DE 10 2007 011 409 A1, during production of enzymatically-broken-down starch paste, starch paste is to be fed to a reaction vessel, in which a turbulent flow is generated. The starch paste is created in a Venturi tube-like agglutination module by the action of the enzyme and steam heating. A method for producing enzymatically-broken-down starch paste is described in DE 10 2007 011 409 A1. In this case, a good mixing of the enzyme with the starch paste in the reaction vessel is to be achieved by turbulent flow. The starch paste is fed to the reaction vessel or produced in the latter. With the stirring mechanism, a more turbulent state is to be created in the reaction vessel in a regulatable manner. In the case of DE 10 2007 011 409 A1, agglutination is carried out—without a stirring mechanism—in an agglutination module, to which steam is fed. Starch paste rather than steam is fed to the reaction vessel.

Figure 3:
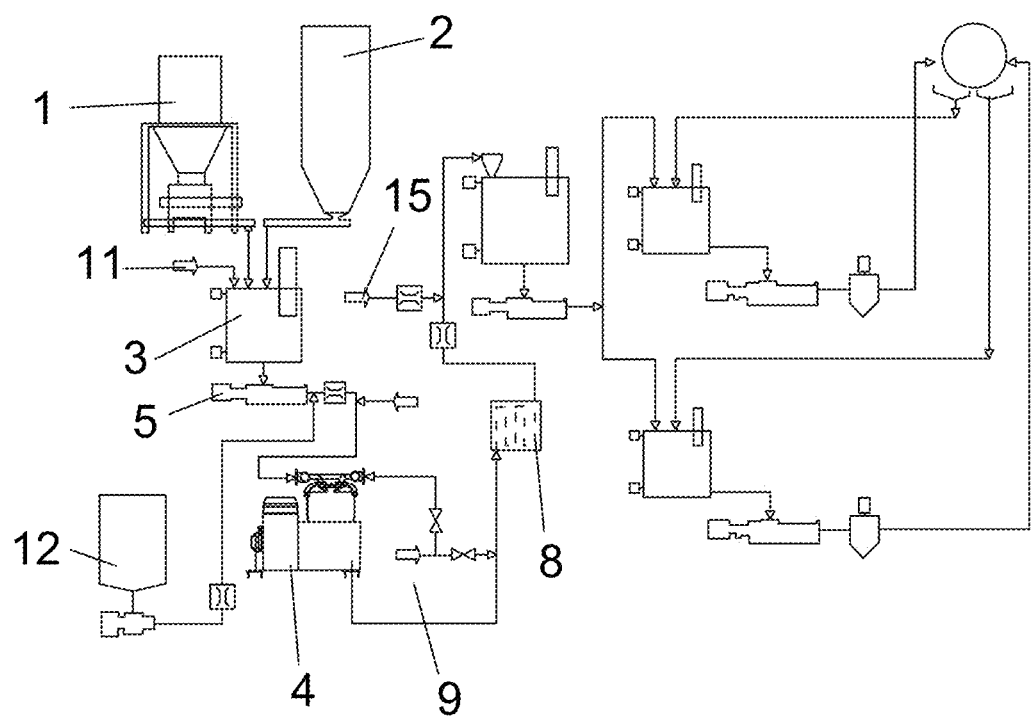

In US 2010/159104 A1, the creation of a colloidal solution of starch in a cooking chamber at a temperature of between 120° C. and 180° C. is described. Paragraph [0021] mentions "breaking of intermolecular hydrogen bonds and dissolution of macromolecules." Paragraph [0039] mentions the introduction of pressurized steam into the colloidal solution of starch in a second step (cf. also paragraph [0066]). It is mentioned in paragraph [0057] that a stirring system is to be used. In the paragraphs [0068] and [0069], it is explained that the introduction of steam "at the base of the chamber" is to be avoided in order to prevent the steam-distributing ring from clogging. With the device that is shown in FIG. 3 of US 2010/159104 A1, steam is fed via lines once to the double wall of the cooker and once to the colloidal solution (paragraphs [0101] and [0102]). This also applies for the cookers that are shown in other figures of US 2010/159104 A1. No reference to steam to be fed in the area of the stirring tool (not identified in more detail) is found in US 2010/159104 A1.

According to U.S. Pat. No. 3,308,037 A, "breakdown products" (decomposition products) of starch, which can be used for gelatinization/enzymatic hydrolysis, are to be produced. It is proposed in U.S. Pat. No. 3,308,037 A to feed steam to a device through a line. The device introduces steam into the boiler from below in FIG. 1 and into the boiler from above in FIG. 2. Stirring mechanisms are not provided in the boilers of U.S. Pat. No. 3,308,037 A.

In the Guglielmo Santi document, a bioreactor with mechanical stirring is proposed, in which saturated steam is to be introduced. Steam is fed through a line that empties into the bottom of the reactor from below. The stirring mechanism ends some distance above the bottom of the reactor.

According to CH 513 980 A, starch milk is subjected to an enzymatic cleavage, wherein the starch milk is agglutinated by heating to 140-150° C. The "paste" that is obtained is cooled and mixed with enzyme and broken down to form maltose syrup. A reaction vessel in the form of a "high-speed mixer" with a rotor and with baffles is to be used. CH 513 980 A thus discloses a method in which starch is agglutinated at 120-160° C. and is cleaved with enzyme in order to create a maltose syrup. The heating of "starch milk" is done with direct or indirect steam heating. A unit for implementing the method with stirring and direct and indirect heating is shown. The stirring mechanism is equipped with blades. Steam is fed into the unit from below in the area of a diffuser. Baffles are arranged above the diffuser, and the stirring mechanism is provided above the baffles. The stirring mechanism that is shown in CH 513 980A is not suitable for creating "shear forces," which is why shear forces also are not mentioned.

SUMMARY OF THE INVENTION

The object of the invention is to make available a method that is improved and that is to be operated more economically for digesting starch and a cooking vessel that can be used when implementing the method.

This object is achieved according to the invention with a method and with a device as disclosed.

With the method according to the invention, it is advantageous that the heating of the slurry (suspension) of starch is carried out directly in a cooking vessel by introducing steam into the cooking vessel and shear forces act on the slurry, so that more advantageous process control is possible.

In particular, in this case, it is preferred that the slurry be heated in the cooking vessel to an agglutination temperature that is between 85° C. and 135° C.

Preferred and advantageous configurations of the procedure according to the invention and the device according to the invention are also disclosed.

With the method according to the invention and the device according to the invention, the known breakdown methods—namely enzymatic starch breakdown, oxidative starch breakdown—are improved by a thermo/mechanical digestion method.

An advantage of the thermo/mechanical starch digestion according to the invention is that in contrast to oxidative and enzymatic methods for digesting starch into paste, no chemical additives are required, so that also only a slight change in molar mass thus occurs. This has in turn the advantage that the thermally-/mechanically-treated native starch has a higher cohesiveness, so that higher paper strengths can be achieved. In addition, because of a slight change in molar mass, a higher yield of starch is achieved.

Another advantage of the invention is due to the fact that with the thermo/mechanical starch digestion according to the invention, no deactivation is required. The term "thermo/mechanical starch digestion" refers to the treatment of starch by the input of heat and by applying shear forces in order to obtain paste.

Advantages of the device proposed according to the invention for carrying out the method according to the invention are that it has a compact design, so that small recirculated quantities and short dwell times are achieved. Another advantage is due to the fact that the method parameters of speed, temperature, stator/rotor design ensure good controllability.

Finally, in the device according to the invention, starch slurries can be processed at high concentration. Another advantage of the device according to the invention is due to the fact that a direct metering of steam in the device is provided, wherein an enzyme—if it is used—can be added in measured quantities according to the device (cooker). With the device according to the invention, significant advantages are achieved relative to conventional starch cookers (pipe cookers, converters, etc.) because of the additionally-introduced mechanical energy (shear forces).

Since, with the device according to the invention, a rotor in combination with a stator is used and at the same time steam is introduced, fast and readily adjustable agglutination of the starch is ensured because of the shear forces that act on the starch slurry. This in turn means that the processing period can be shortened. Another advantage is that many types of starch (e.g., corn, wheat, potato) can be processed.

When, in the device according to the invention, an increased reaction temperature (cooking temperature) is applied, a reduction in the viscosity of the starch paste that is created and more stable operation are achieved.

Because of the mechanical shearing input, a reduction in rough colloidal starch particles is achieved, which is responsible for a reduction in the viscosity of the starch paste that is created.

By selecting the form of the rotor of the device according to the invention (height and diameter of the rotor and its speed), the viscosity of the starch paste that is created can be set.

It is an advantage of the method for digesting starch according to the invention that at least one enzyme can be added to the paste that is obtained by the digestion in order to create a product that is usable in, e.g., the paper industry by enzymatic breakdown and the thus designed setting of the desired low viscosity of the paste.

When an enzyme is used with the method according to the invention, the latter is rendered inactive by deactivation either in the method or in the completion of the method.

In a possible embodiment, the method according to the invention can be distinguished in that steam from a hollow displacement element, which is arranged in the cooking vessel, exits through at least one outlet opening for steam in the area of the rotor.

In a possible embodiment, the method according to the invention can be distinguished in that the starch-containing slurry is heated to a temperature of between 85° C. and 135° C. in the cooking vessel in step c) by introducing steam.

In a possible embodiment, the method according to the invention can be distinguished in that step c) is implemented during a time span of 1 to 5 hours.

In a possible embodiment, the method according to the invention can be distinguished in that in step a), a slurry with at most 35-45% starch powder is created as a solid.

In a possible embodiment, the method according to the invention can be distinguished in that the slurry before step b) is heated to a temperature of between 85° C. and 95° C.

In a possible embodiment, the method according to the invention can be distinguished in that when implementing step c), the degree of digestion of starch is set by selecting the speed at which the slurry is stirred in the cooking vessel.

In a possible embodiment, the method according to the invention can be distinguished in that when implementing step c), the degree of digestion of starch is set by selecting the throughput of the slurry.

In a possible embodiment, the method according to the invention can be distinguished in that when implementing step c), the degree of digestion of starch is set by selecting the temperature of the slurry.

In a possible embodiment, the method according to the invention can be distinguished in that after step d), the enzyme is deactivated.

In a possible embodiment, the method according to the invention can be distinguished in that the deactivation of the enzyme is carried out by heating the paste to a temperature of between 120° C. and 135° C.

In a possible embodiment, the method according to the invention can be distinguished in that the temperature is increased by introducing steam.

In a possible embodiment, the method according to the invention can be distinguished in that the throughput of slurry through the cooking vessel is regulated in step c) by obstructing the flow of slurry through the cooking vessel and/or by static mixing of the slurry in or behind the cooking vessel.

In a possible embodiment, the method according to the invention can be distinguished in that in step a), cationic starch powder is used in order to create the slurry.

In a possible embodiment, the method according to the invention can be distinguished in that in step a), native starch powder is used in order to create the slurry.

In a possible embodiment, the device according to the invention can be distinguished in that the steam feed line empties into the hollow displacement element and in that the displacement element has at least one outlet opening for steam on its side that is opposite to the emptying point of the line and adjacent to the rotor.

In a possible embodiment, the device according to the invention can be distinguished in that the outlet openings are provided in a distributed manner over the annular end surface, facing the rotor, of the displacement element.

In a possible embodiment, the device according to the invention can be distinguished in that the steam feed line empties into a hollow ring with at least one outlet opening for steam.

In a possible embodiment, the device according to the invention can be distinguished in that the ring is arranged on the side of the rotor that turns away from the displacement element.

In a possible embodiment, the device according to the invention can be distinguished in that the outlet opening is provided in the wall of the ring that faces the rotor.

In a possible embodiment, the device according to the invention can be distinguished in that the ring has multiple outlet openings that are arranged in a distributed manner over its extension.

In a possible embodiment, the device according to the invention can be distinguished in that the stator sheets protrude from the displacement element and project to the inside surface of the container.

In a possible embodiment, the device according to the invention can be distinguished in that the rotor has fins at least on one of its sides.

In a possible embodiment, the device according to the invention can be distinguished in that the opening of the displacement element that is coaxial to the shaft of the rotor is funnel-shaped, wherein the broadened area of the opening faces toward the cover of the container.

In a possible embodiment, the device according to the invention can be distinguished in that the axis of the line is oriented coaxial with the annular displacement element and with the rotor.

In a possible embodiment, the device according to the invention can be distinguished in that the fins on the dispersing disk increase in height from the inside to the outside.

In a possible embodiment, the device according to the invention can be distinguished in that the fins are set obliquely to the radial planes, which pass through the shaft of the rotor.

In a possible embodiment, the device according to the invention can be distinguished in that the rotor projects through the bottom of the container into the interior of the container.

In a possible embodiment, the device according to the invention can be distinguished in that in the area of the emptying point of the line, a constriction that acts as a diffuser is provided.

In a possible embodiment, the device according to the invention can be distinguished in that the constriction is formed by an annular fin, in particular an annular fin with a triangular cross-section.

DESCRIPTION OF THE PREFERRED EMBODIMENTS

Figure 2:
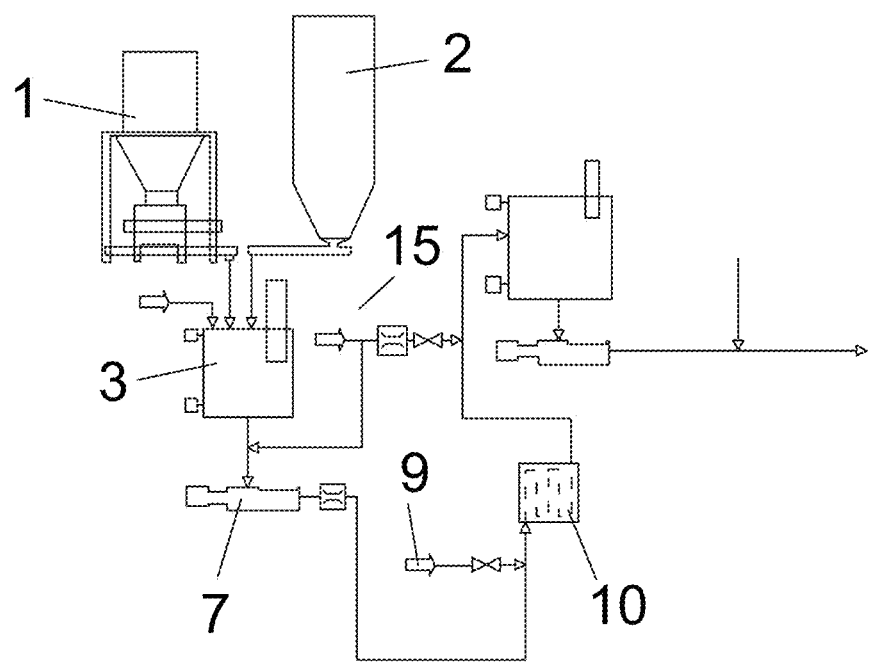
Figure 4:
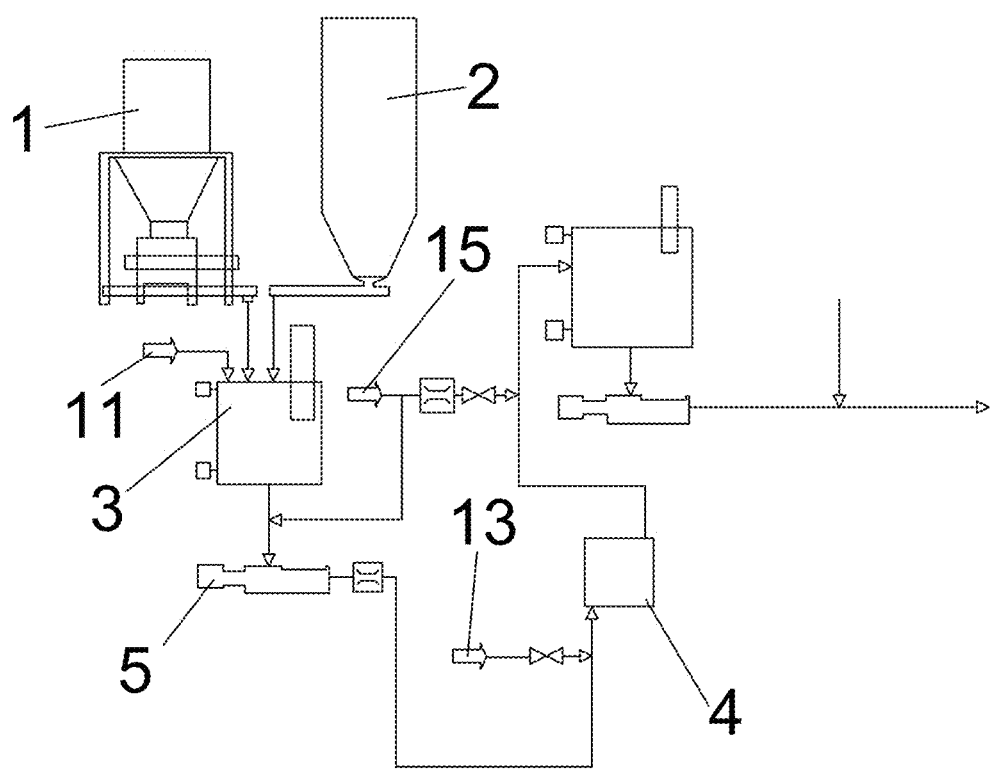
Figure 5:
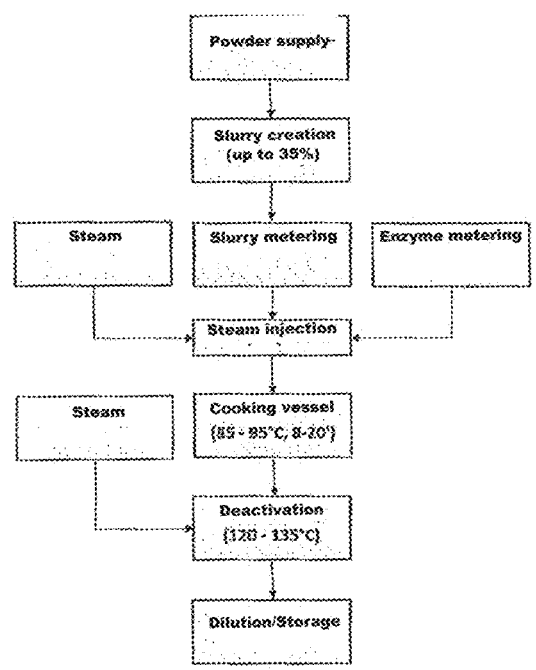
Figure 6:
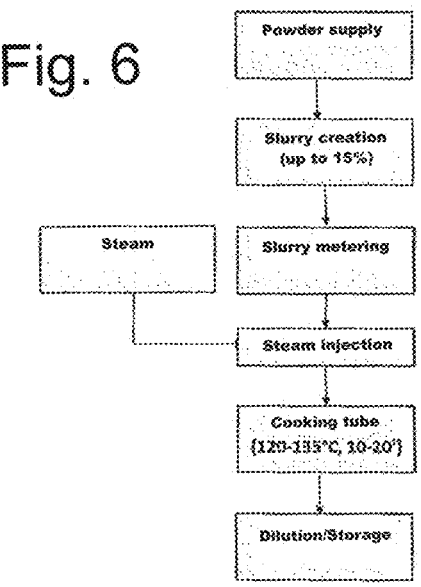
Figure 7:
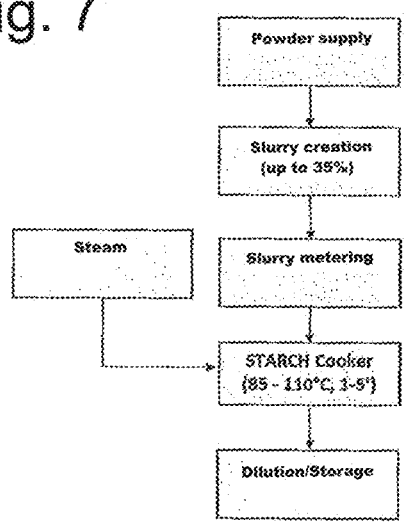
Figure 8:
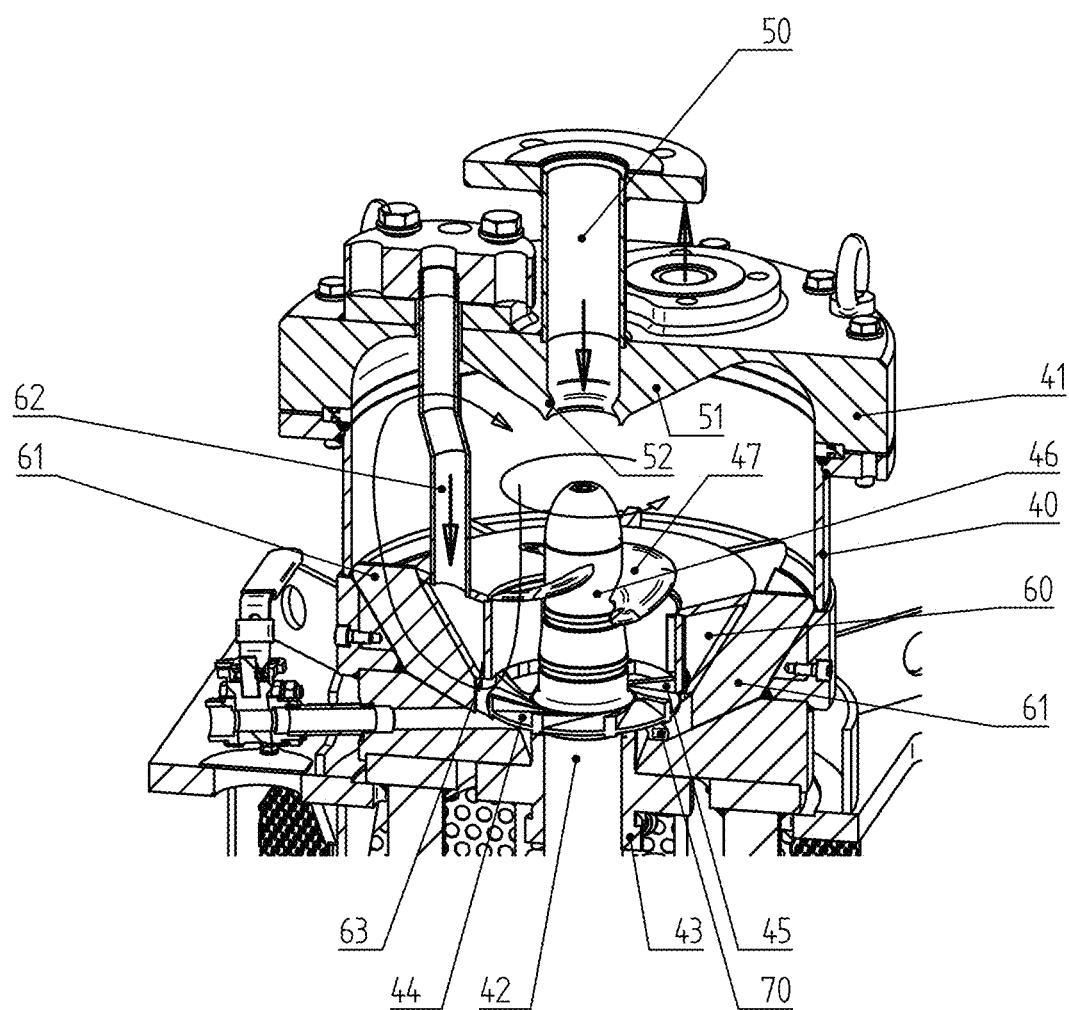
Figure 9:
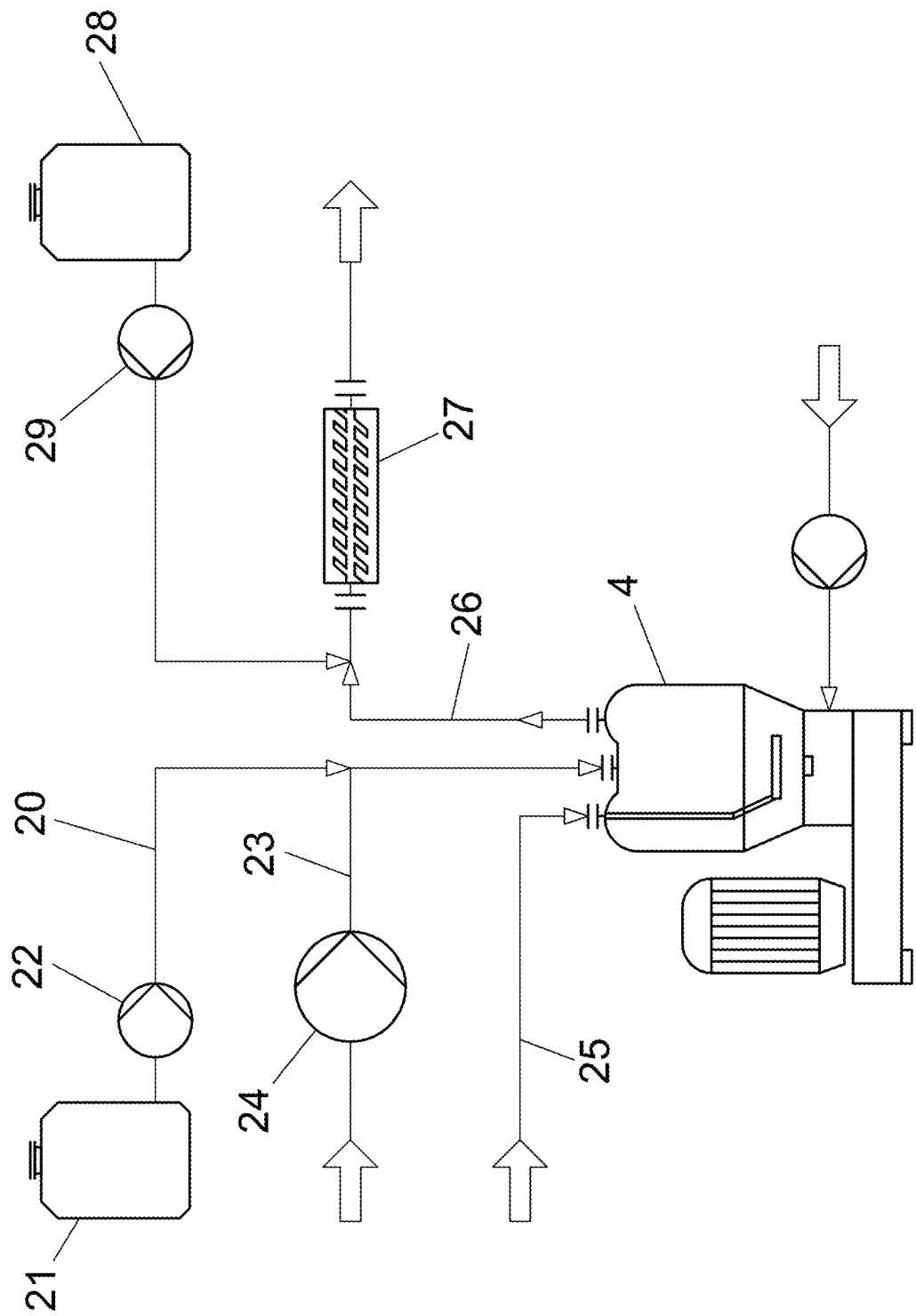
Figure 10:
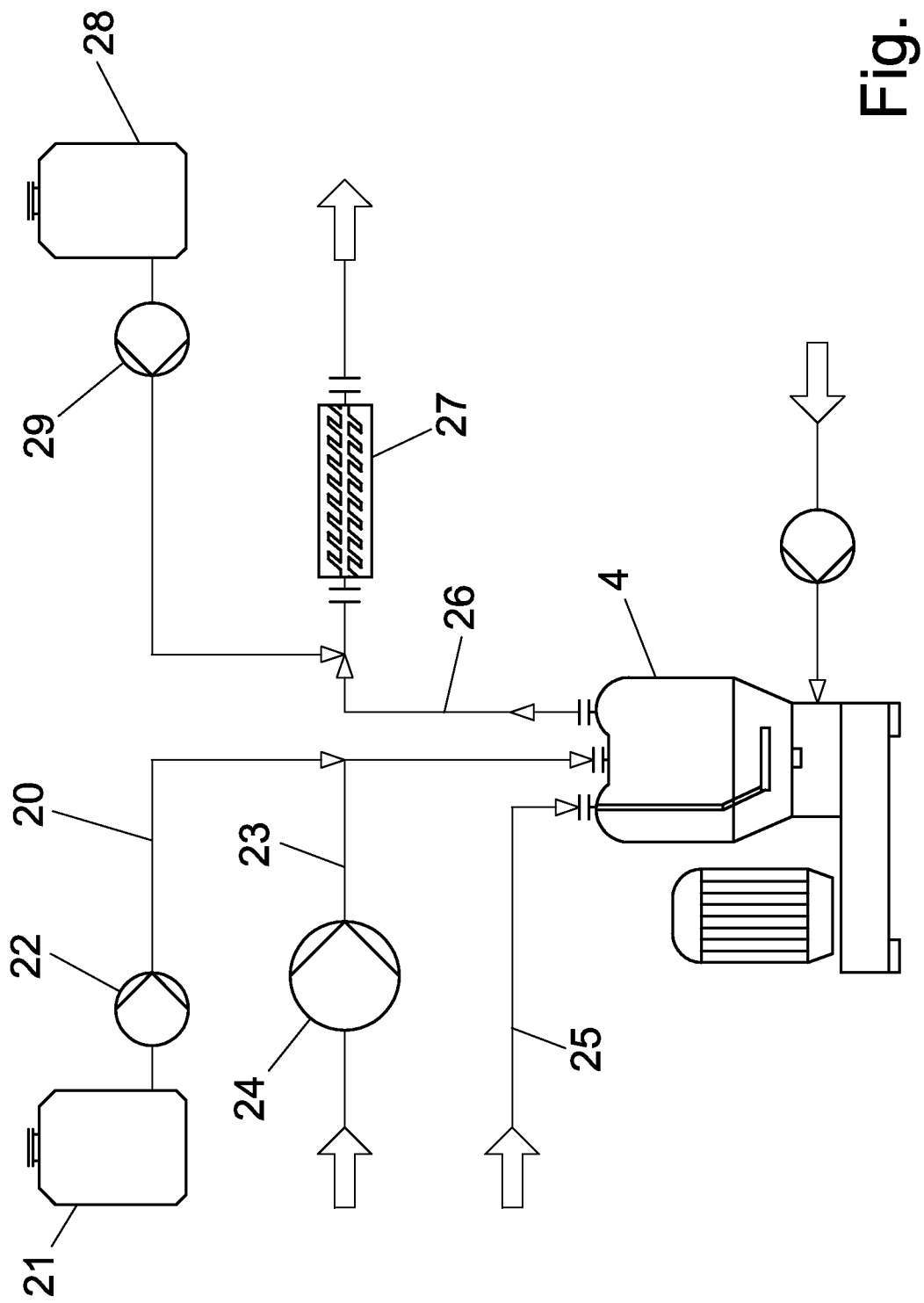

Additional details and features of the invention are given in the description below with reference to the drawings, in which known units and procedures, procedures according to the invention and units according to the invention as well as a cooking vessel that can be used according to the invention are depicted by way of example. Here:

FIG. 1 shows diagrammatically a (known) unit for enzymatic breakdown of native starch, FIG. 2 shows diagrammatically a (known) unit for digesting cationic starch, FIG. 3 shows a unit for carrying out a (continuous) method for enzymatic breakdown of native starch, FIG. 4 shows a unit for implementing the method according to the invention for digesting cationic starch, FIG. 5 shows, in a block diagram, a known method for the enzymatic breakdown of starch, FIG. 6 shows, in a block diagram, a known method for digesting cationic starch, FIG. 7 shows, in a block diagram, a method according to the invention for digesting cationic starch, FIG. 8 shows, partially and in section, two embodiments of a cooking vessel, which can be used when implementing the method according to the invention, and FIG. 9 shows a unit that is also suitable for implementing the method according to the invention.

DESCRIPTION OF THE PREFERRED EMBODIMENTS

The known method for starch that is to be broken down enzymatically, which method can be implemented continuously in a unit according to FIG. 1 and according to the block diagram of FIG. 5, can be described as follows:

Used as raw components are:
Native starch powder,
Water,
Steam, and
Enzyme (amylase).

Starch powder is stored in BigBags 1 or silos 2. From this supply, the starch powder is fed into the slurry station 1. In this station 3, the starch powder is introduced into water, and a slurry (suspension) with up to 35% solid content is created. From there, the slurry (starch suspension) is pumped using a pump 5 into a cooking vessel 4. The enzymes can be added in measured quantities from a supply container 6 in the slurry station 3, in front of or behind the pump 5. In most units, before it enters the cooking vessel 4, the slurry is brought to the agglutination temperature (85° C. to 95° C.) by means of steam injection 9.

In addition, static mixers or other components can be installed in the feed of the cooking vessel 4 in order to prevent the slurry from shooting through and to configure the feed to be homogeneous. In the actual cooking vessel 4, the necessary dwell time (8 to 20 minutes) for the desired degree of breakdown is set by means of volume buffering. In the cooking vessel 4, stirring mechanisms and/or mixer-disks are installed in order to accelerate the breakdown process, by shear forces being brought into the slurry in the cooking vessel 4.

By means of a pump 7, paste is continuously drawn off from the cooking vessel 4 and pumped through a deactivation zone 8. The deactivation zone 8 is a plug flow reactor, in which the paste is heated to 120° C. to 135° C. at the beginning by means of steam injection 9, wherein the deactivation time can be controlled by the pipe volume and/or the pumping power. After the breakdown process is stopped, the paste that is obtained is optionally diluted with water from a line 15 and then stored.

It is known to provide a labyrinth pipe instead of the cooking vessel 4 after the steam injection, in which pipe firstly the necessary dwell time can be achieved and secondly, via shear edges, an additional shearing of the slurry is achieved.

The cooking vessel can—when it is made accordingly large enough—also be used in batch operation. Then, all method steps are run starting from the production of suspension in the cooking vessel 4. The drawback is that relatively large units are necessary or accordingly small throughput amounts can be run.

With the known method of a cooking process for cationic starch, which can be carried out in a unit according to FIG. 2 and which can flow as indicated in the block diagram of FIG. 7, it is possible to proceed as follows:

Used as raw components are:
Cationic starch powder,
Water, and
Steam.

Starch powder is stored in BigBags 1 or silos 2. The slurry station 3 is fed from this supply. In this station 3, the powder is introduced into water, and a slurry (suspension) with up to 15% solid content is created. From there, the starch suspension is pumped into the cooking tube 10.

The cooking tube 10 is a plug flow reactor, in which the starch suspension is heated to 115° C. to 135° C. at the beginning by means of steam injection 9, wherein the dwell time can be controlled by the pipe volume and/or the pumping power. After the cooking process, the paste that is obtained (digested starch) is optionally diluted again (water from line 15) and then stored.

It is known to provide a labyrinth pipe instead of the cooking tube 10 after the steam injection 9, in which pipe firstly the necessary dwell time can be achieved and secondly, via shear edges, an additional shearing of the slurry is achieved.

The cooking tube can be replaced by a cooking vessel 10. When it is made accordingly large enough, the cooking vessel 10 can also be used in batch operation. Then, all method steps are run starting from the production of suspension in the cooking vessel 10. The drawback is that relatively large units are necessary, or accordingly small throughput amounts can be run.

A method for digesting cationic starch according to the invention can be carried out in a unit, which is shown in FIG. 4 and uses a cooking vessel according to FIG. 8, wherein the method can flow as indicated in the block diagram according to FIG. 7. In detail, in this case, it is possible to proceed as follows:

Used as raw components are:
Cationic starch powder,
Water, and
Steam.

Starch powder is stored in BigBags 1 or silos 2. The slurry station 3 is fed from this supply. In this station 3, the powder is introduced into water from the line 11, and a slurry (suspension) with up to 35% solid content is created. From there, the starch suspension is pumped with the pump 5 into the cooker 4.

The steam injection is carried out via a line 13 directly into the cooker 4, where the slurry is brought to the agglutination temperature (85° C. to 135° C.).

In addition, static mixers or other components can be installed after the fact, in order to prevent the slurry from shooting through the cooker 4 and/or to configure the cooking process to be more homogeneous. In the cooker 4, the desired starch properties can be set by means of a change in speed, a change in throughput, and/or the cooking temperature.

The paste that is obtained is optionally diluted with water from the line 15 and then stored.

A device (cooker 4), which can be used for digesting cationic starch when implementing the method according to the invention, can have the design that is shown in FIG. 8.

A device according to the invention that is used as the cooking vessel 4 comprises a container 40, which is closed on its top by a cover 41. In the container 40, a rotor 42, which is mounted in a bearing body (not shown) that is arranged below the container 40, projects from below.

The feedthrough of the rotor 42 into the container 40 is sealed by sliding-ring seals 43.

The rotor 42 is mounted in the bearing body by roller bearings (not shown).

In its part that is arranged in the lower area of the container 40, the rotor 42 has a dispersing disk 44, which on its top has fins 45 that are tilted relative to the radial direction. In this case, the orientation of the fins 45 relative to the direction of rotation of the rotor 42 in an embodiment is selected so that the radial inner ends of the fins 45, relative to the direction of rotation, lie further forward than the radial outer ends of the fins.

In a modified embodiment, the fins 45 are oriented so that their radial outer ends, relative to the direction of rotation, lie further back than their radial inner ends.

Moreover, the fins 45 can increase in height from the inside to the outside.

The fins 45 are, for example, curved on the top of the dispersing disk 44. Curved fins 45 are oriented either so that the convex side of the fins 45 points toward the front relative to the direction of rotation of the dispersing disk 44 or so that the convex side points toward the rear relative to the direction of rotation of the dispersing disk 44.

The fins 45 on the top of the dispersing disk 44 can thus also be curved, so that the concave side of the fins 45 points toward the front or toward the rear relative to the direction of rotation of the dispersing disk 44.

The fins 45 on the top of the dispersing disk 44 can also be straight fins.

Because of the rotating rotor 42, which is provided in the cooking vessel 40 (cooker), with the dispersing disk 44, shear forces are brought into the slurry of starch introduced into the container 40, thereby advantageously supporting the digestion of starch.

The rotor 42 has, for example, a diameter of 100 to 150 mm, preferably 130 mm, and—including the fins 45 on the dispersing disk 44—a height of, for example, 3 to 10 mm, in particular 5 to 7 mm. The rotor 42 is rotated at, for example, a speed of between 3,000 and 5,000 rpm. The speed of the rotor 42 is selected based on its diameter in order to reach the necessary circumferential speed.

On the rotor 42, a propeller 46 with blades 47 is provided above the dispersing disk 44; in the suspension that is to be prepared, the propeller creates a flow that is directed downward onto the dispersing disk 44. The propeller 46 is not necessarily provided.

In the cover 41, a line 50, through which the suspension flows into the container 40, empties coaxially to the rotor 42.

On the inside of the cover 41, a cone-shaped projection 51 that points inward is provided, a projection into whose center the suspension feed line 50 empties.

This arrangement of the line 50 ensures an optimal mixing of the suspension, which is located in the circuit in the container 40 with suspension that is newly fed into the container 40.

Because at the end of the line 50 (emptying point in the container 40), there is a constriction 52 acting as a diffuser (formed by an annular fin that is triangular in cross-section), the above-mentioned mixing of the fed suspension with suspension that is already in the container 40 and is being prepared is advantageously supported.

Drain lines (or at least one) encircling the feed line 50 are provided for draining prepared suspension (digested starch).

The cover 41 is screwed to the container 40.

In the inside space of the container 40, an annular displacement element 60 is provided, whose inner opening can be designed approximately funnel-shaped. Between the outside surface of the displacement element 60 and the inside of the wall of the container 40, an annular channel is located, in which suspension flows upward after leaving the dispersing disk 44. Suspension, optionally supported by the propeller 45 on the rotor 42, flows through the inner opening of the displacement element 60 downward in the direction toward the dispersing disk 44.

In the embodiment that is shown, the upper end of the rotor 42 is covered by an aerodynamically-efficient covering that is fixed in the rotor 42 using a socket screw.

On the outside of the displacement element 60, stator sheets 61, which span the annular channel (gap) between the outside of the displacement element 60 and the inside of the wall of the container 40 (in particular in its lower part), i.e., with its free edges adjoin the inside of the wall of the container 40, are provided as baffles.

In order to hold the displacement element 60 in the interior of the container, fastening screws can be provided.

With the embodiment of the cooking vessel 4 that is shown on the left in FIG. 8, the displacement element 60 is hollow and is fed with steam via a line 62, which is guided through the cover 41 of the housing 40 of the cooking vessel 4. The line 62 empties into the upper end surface of the hollow displacement element 60. On its bottom, the displacement element 60—distributed around the inner opening of the displacement element 60—has multiple outlet openings 63, so that steam that is introduced via the line 62 into the inside space of the displacement element 60 can exit into the inside space of the container 40 in the area of the rotor 42, in particular in the area of its dispersing disk 44.

In the embodiment that is shown on the right in FIG. 8, a hollow ring 70 (diffuser ring) is provided, in which ring openings are provided for the discharge of steam. As shown on the right in FIG. 9, the ring 70 is arranged on the side of the dispersing disk 44 of the rotor 40 that turns away from the displacement element 60, wherein the outlet openings in the ring 70 are directed upward, i.e., in the direction toward the displacement element 40. For the sake of clarity, the line via which steam is fed to the ring 70 is not depicted in FIG. 9.

For certain applications, it can be advantageous for the feeding of steam into the inside space of the container 40 of the cooking vessel 4 to be carried out both via the hollow displacement element 60 and via the ring 70.

In the case of the unit for starch preparation (digestion of starch) shown in FIG. 9, starch is agglutinated without enzyme being added in the starch-dispersing cooker (e.g., cooking vessel 4). After agglutination, enzyme is added in measured quantities to the paste according to the output of the starch cooker and is worked homogeneously using a static mixer. After a variable dwell time, by means of corresponding pipework, the enzyme is deactivated by increasing the temperature. In this case, the advantage is that a) The starch is agglutinated with almost no molecular weight reduction in the starch-dispersing cooker (e.g., cooking vessel 4), and b) With the subsequent enzyme treatment, the starch properties, such as viscosity and degree of digestion, can be set individually to customer needs.

Moreover, subsequent use can also be influenced by the shear energy input in the starch-dispersing cooker (e.g., cooking vessel 4).

FIG. 9 shows a unit in which the previously-described embodiment of the method according to the invention can be implemented.

The unit that is shown in FIG. 9 comprises a cooking vessel 4 ("starch-dispersing cooker"), which can be designed like the cooking vessel 4 that is shown in FIG. 8. A line 20, through which enzyme is fed from an enzyme supply container 21 using a pump 22, empties into the cooking vessel 4 (not in accordance with the invention).

Using a pump 24, starch is conveyed into the cooking vessel 4 via another line 23.

Steam is introduced into the cooking vessel 4 through a line 25.

Starch that is digested to form paste is drawn off from the cooking vessel 4 via a line 26. Enzyme is admixed from a supply container 28 (using a pump 29) in front of a static mixer 27.

Water as sealing water for the sliding-ring seal 43 can be fed into the lower area of the cooking vessel 4 via a line 30 that is supported by a pump 31.

Below, examples of the method according to the invention are reproduced:

EXAMPLE 1

Wheat starch (Collamyl 7411) with 13% moisture is mixed with water in order to create a slurry with 30% by weight of content of wheat starch. The slurry thus obtained was agglutinated with a throughput of 750 l/h at a cooking temperature of 115° C. in a device according to FIG. 9. Immediately behind the device according to FIG. 9, the enzyme V Warozym A152 was added in measured quantities in front of a static mixer in a constant amount of 4.28 l/h. The rotor 42 used in the device according to FIG. 9 had a height of 7 mm.

At a rotor speed of 4,200 rpm with a rotor 42, whose diameter was 130 mm, a paste with a viscosity of 12,500 mPas was created, with the motor driving the rotor 42 having a power consumption of 35 amperes.

EXAMPLE 2

The procedure was carried out as indicated in Example 1, wherein the rotor speed was increased to 4,400 rpm, and the power consumption of the motor was 41 amperes. A paste with a viscosity of 9,700 mPas was created.

EXAMPLE 3

The procedure was carried out as in Example 1, wherein the rotor speed was increased to 4,400 rpm, and the enzyme was added in the amount of 2.14 l/h. A paste with a viscosity of 9,500 mPas was created.

EXAMPLE 4

The procedure was carried out as indicated in Example 3, wherein the amount of enzyme added was increased to 4.28 l/h. A paste with a viscosity of 7,800 mPas was created.

EXAMPLE 5

The procedure was carried out as indicated in Example 3, wherein the amount of enzyme added was increased to 8.56 l/h. A paste with a viscosity of 7,400 mPas was created.

EXAMPLE 6

The procedure was carried out as indicated in Example 1, wherein the procedure was carried out at a rotor speed of 4,400 rpm and a rotor 42 with a diameter of 130 mm. The reaction temperature was set at 100° C., with the motor driving the rotor 42 having a power consumption of 38 amperes. The paste that was obtained had a viscosity of 13,950 mPas.

EXAMPLE 7

The procedure was carried out as indicated in Example 6, wherein a reaction temperature was set at 115° C. The power consumption of the motor was 35 amperes. The paste had a viscosity of 9,700 mPas.

EXAMPLE 8

The procedure was carried out as indicated in Example 1, wherein the reaction temperature was 115° C., and the rotor 42 operated at a speed of 4,400 rpm. The rotor 42 had a diameter of 130 mm and a height of 5 mm. The power consumption of the motor was 37 amperes. A viscosity of the paste of 10,700 mPas was achieved.

EXAMPLE 9

The procedure was carried out as indicated in Example 8, wherein a rotor 42 with a height of 7 mm was used, and the power consumption of the motor was 41 amperes. As a result, a paste with a viscosity of 9,700 mPas was created.

EXAMPLE 10

Potato starch (Collamyl 9100) with 13% moisture was brought into water in order to obtain a slurry with 20% by weight of potato starch. The slurry thus obtained was agglutinated with a throughput of 750 l/h at 115° C. in a device according to FIG. 9. The enzyme from Example 1 was added behind the device according to FIG. 9 but also in front of the static mixer.

The slurry that exits from the device according to FIG. 9 was routed through a plug flow reactor with a reaction length of 7,500 mm. As a result, a paste with a viscosity of 1,660 mPas was created, and the starch paste created was clear and optimally dissolved.

EXAMPLE 11

The procedure was carried out as in Example 10, with the proviso that the reaction length of the plug flow reactor was 10,000 mm. The viscosity of the starch paste created was 1,540 mPas. The starch paste was clear, and the starch was optimally dissolved.

EXAMPLE 12

The procedure was carried out as in Example 10, wherein a slurry of 25% by weight of potato starch was used. The starch paste created was clear, and the starch was optimally dissolved.

EXAMPLE 13

Wheat starch with a moisture of 13% was mixed with water to form a 30% slurry and cooked at 98° C. in a device according to FIG. 9. The height of the rotor in the device according to FIG. 9 was 7 mm. The enzyme (Warozym A152) was added in measured quantities directly behind the device according to FIG. 9, and after the slurry exited from the device according to FIG. 9, a temperature of 95° C. was maintained. Then, post-dilution was done with 60° C. water and a throughput of 240 l/h. At a constant rotor speed of 4,200 rpm and an addition of enzyme of 1,400 ml/h, a viscosity of the paste of 440 mPas could be achieved.

EXAMPLE 14

The procedure was carried out as in Example 13, wherein an addition of enzyme was applied in the amount of 1,800 ml/h. The viscosity of the starch paste that was obtained was 240 mPas.

EXAMPLE 15

The procedure was carried out as in Example 13, wherein the amount of enzyme added was increased to 2,200 ml/h. The viscosity of the starch paste obtained was 140 mPas.

EXAMPLE 16

The procedure was carried out as in Example 13, wherein a rotor speed of 3,800 rpm and a rotor with a diameter of 130 mm were used. A viscosity of the paste of 580 mPas was achieved.

EXAMPLE 17

The procedure was carried out as in Example 17, wherein a rotor speed of 4,200 rpm has been applied. A starch paste with a viscosity of 270 mPas was created.

EXAMPLE 18

The procedure was carried out as in Example 16, wherein the rotor speed was increased to 4,800 rpm. A viscosity of the starch paste of 250 mPas was achieved.

EXAMPLE 19

The procedure was carried out as in Example 16, wherein a rotor speed of 5,000 rpm has been applied. The starch paste created had a viscosity of 180 mPas.

EXAMPLE 20

Cationized potato starch (Cationamyl 9853K) was mixed with water to form a slurry with 7.5% potato starch. The slurry thus obtained was cooked at 98° C. with a throughput of 500 l/h in a device according to FIG. 9 and then post-diluted to a 4% content. In this example, better digestion was achieved with higher consistency because of the inner friction. This could be ascertained visually by examination by microscope.

EXAMPLE 21

A slurry with 15% content of potato starch was processed as in Example 20, wherein it was cooked at 110° C. in the device according to FIG. 9. With higher paper strengths, the starch paste achieved a lower porosity, which was ascertained by means of a lab sheet.

In summary, an embodiment of the invention can be described as follows:

With a method for digesting starch (native starch or processed starch, such as cationic starch), an aqueous slurry of the starch is treated with steam in a cooking vessel 4 and in this case exposed to shear forces, wherein the starch-containing slurry is heated to a temperature of between 85° C. and 110° C. in the cooking vessel 4 by introducing steam, and the digestion step is implemented until the desired degree of digestion has been reached.

The invention claimed is:

1. Method for digesting starch, comprising:
   a) Creating an aqueous slurry of powdery starch,
   b) Introducing the slurry into a cooking vessel (4),
   c) Treating the slurry in the cooking vessel (4) with steam, by: using a rotor with a finned dispersing disk to expose the slurry by mechanical action to shear forces that are created by the rotor with the finned dispersing disk, and implementing thermomechanical digestion by feeding steam from openings of at least one of a hollow ring (70) and a hollow displacement element, arranged below the rotor, the openings being directed toward the rotor (42) for the discharge of the steam toward the rotor, in order to implement the thermomechanical digestion, and
   d) Drawing off the starch, converted at least partially into paste, from the cooking vessel (4).

2. The method according to claim 1, wherein steam exits from the hollow displacement element (60), which is arranged in the cooking vessel (4), through at least one outlet opening (63) for steam in the area of the rotor (42).

3. The method according to claim 1, wherein the starch-containing slurry is heated to a temperature of between 85° C. and 135° C. in the cooking vessel (4) in step c) by introducing steam.

4. The method according to claim 1, wherein step c) is implemented during a time span of 1 to 5 hours.

5. The method according to claim 1, wherein in step a), a slurry with at most 35-45% starch powder is created as a solid.

6. The method according to claim 1, wherein the slurry is heated before step b) to a temperature of between 85° C. and 95° C.

7. The method according to claim 1, wherein when implementing step c), the degree of digestion of starch is set by selecting the speed at which the slurry is stirred in the cooking vessel.

8. The method according to claim 1, wherein when implementing step c), the degree of digestion of starch is set by selecting the throughput of the slurry.

9. The method according to claim 1, wherein when implementing step c), the degree of digestion of starch is set by selecting the temperature of the slurry.

10. The method according to claim 1, wherein the throughput of slurry through the cooking vessel (4) is regulated in step c) by obstructing the flow of slurry through the cooking vessel (4) and/or by static mixing of the slurry in or behind the cooking vessel (4).

11. The method according to claim 1, wherein in step a), cationic starch powder is used in order to create the slurry.

12. The method according to claim 1, wherein in step a), native starch powder is used in order to create the slurry.

13. The method according to claim 1, wherein enzyme is added to the paste that is obtained according to step d) and wherein starch that is contained in the paste is broken down under the action of enzyme.

14. The method according to claim 13, wherein the enzyme is deactivated.

15. The method according to claim 14, wherein the deactivation of the enzyme is carried out by heating the paste to a temperature of between 120° C. and 135° C.

16. The method according to claim 15, wherein the temperature is increased by introducing steam.

\* \* \* \* \*